United States Patent
Glickman et al.

(10) Patent No.: US 10,910,120 B2
(45) Date of Patent: Feb. 2, 2021

(54) CLOTHING OR ACCESSORY FOR PROTECTION AGAINST IONIZING RADIATION

(71) Applicant: Barrier Technologies, LLC, Davie, FL (US)

(72) Inventors: Marc E. Glickman, Davie, FL (US); Eric Sitbon, Paris (FR); Ruben Sitbon, Paris (FR)

(73) Assignee: Barrier Technologies, LLC, Davie, FL (US)

( * ) Notice: Subject to any disclaimer, the term of this patent is extended or adjusted under 35 U.S.C. 154(b) by 0 days.

(21) Appl. No.: 16/674,407

(22) Filed: Nov. 5, 2019

(65) Prior Publication Data

US 2020/0194138 A1 Jun. 18, 2020

Related U.S. Application Data

(63) Continuation-in-part of application No. 15/843,563, filed on Dec. 15, 2017, now Pat. No. 10,463,088.

(30) Foreign Application Priority Data

Jul. 6, 2017 (FR) .................................... 17 56381

(51) Int. Cl.
   *G21F 3/03* (2006.01)
   *A61B 6/10* (2006.01)
(52) U.S. Cl.
   CPC ................ *G21F 3/03* (2013.01); *A61B 6/107* (2013.01)
(58) Field of Classification Search
   USPC .................................................... 250/516.1
   See application file for complete search history.

(56) References Cited

U.S. PATENT DOCUMENTS

| | | | |
|---|---|---|---|
| 4,938,233 A | * | 7/1990 | Orrison, Jr. ............... G21F 1/10 128/849 |
| 5,274,889 A | * | 1/1994 | Morita .................... A41F 1/002 24/303 |

(Continued)

FOREIGN PATENT DOCUMENTS

| | | |
|---|---|---|
| FR | 2786669 | 6/2000 |
| WO | WO2014071022 | 5/2014 |

OTHER PUBLICATIONS

Notice of Abandonment dated Feb. 28, 2007 received for U.S. Appl. No. 10/501,612.

*Primary Examiner* — Phillip A Johnston
(74) *Attorney, Agent, or Firm* — Jon Gibbons; Fleit Intellectual Property Law

(57) ABSTRACT

It is a clothing or accessory for protection against ionizing radiation comprising a body of flexible material threadable by an operator and reinforcing protection means comprising of one or more layers or plates protecting against ionizing radiation integrated within said body. The garment comprises at least two parts, each provided with a magnetic element for setting, adjusting, arranging or closing the garment or accessory when one of the parts is activated by the operator to cooperate with the other part. Each magnetic element is composed of at least two groups each comprising at least one positive magnet and at least one negative magnet, the groups of the same magnetic element being set directly or indirectly on the same support and/or between them and being able to co-operate with the groups of opposing polarities of the other magnetic element.

15 Claims, 18 Drawing Sheets

(56) References Cited

U.S. PATENT DOCUMENTS

| | | | |
|---|---|---|---|
| 6,841,791 B2* | 1/2005 | DeMeo | B32B 5/26 |
| | | | 250/515.1 |
| 7,488,963 B2* | 2/2009 | Lagace | G21F 1/106 |
| | | | 250/515.1 |
| 8,505,174 B2* | 8/2013 | Fildan | A41F 1/006 |
| | | | 24/303 |
| 9,754,690 B2* | 9/2017 | Rebar | G21F 1/106 |
| 10,463,088 B2* | 11/2019 | Glickman | A43B 1/0054 |
| 2005/0102802 A1 | 5/2005 | Sitbon | |
| 2015/0004131 A1 | 1/2015 | Milstein et al. | |

* cited by examiner

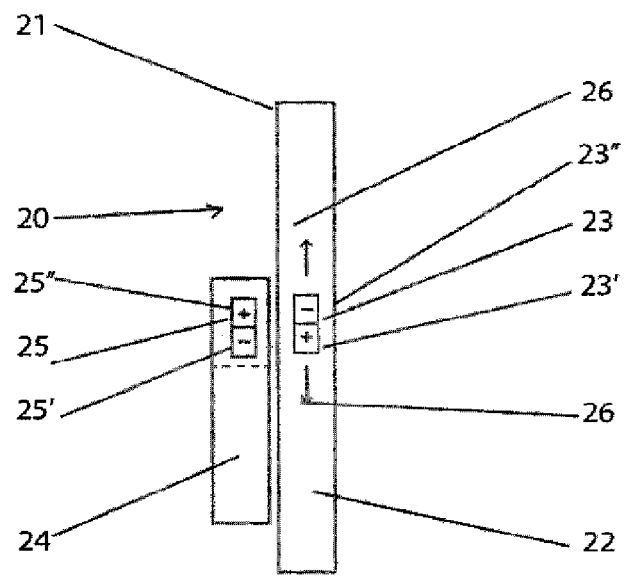
FIG 2
FIG 3
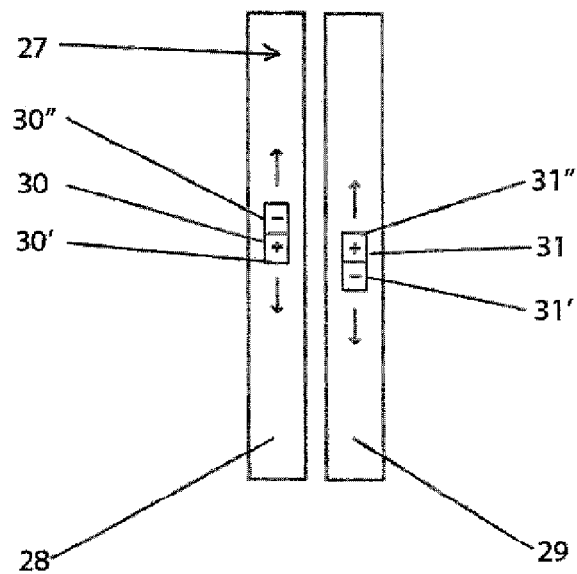

Figure 10
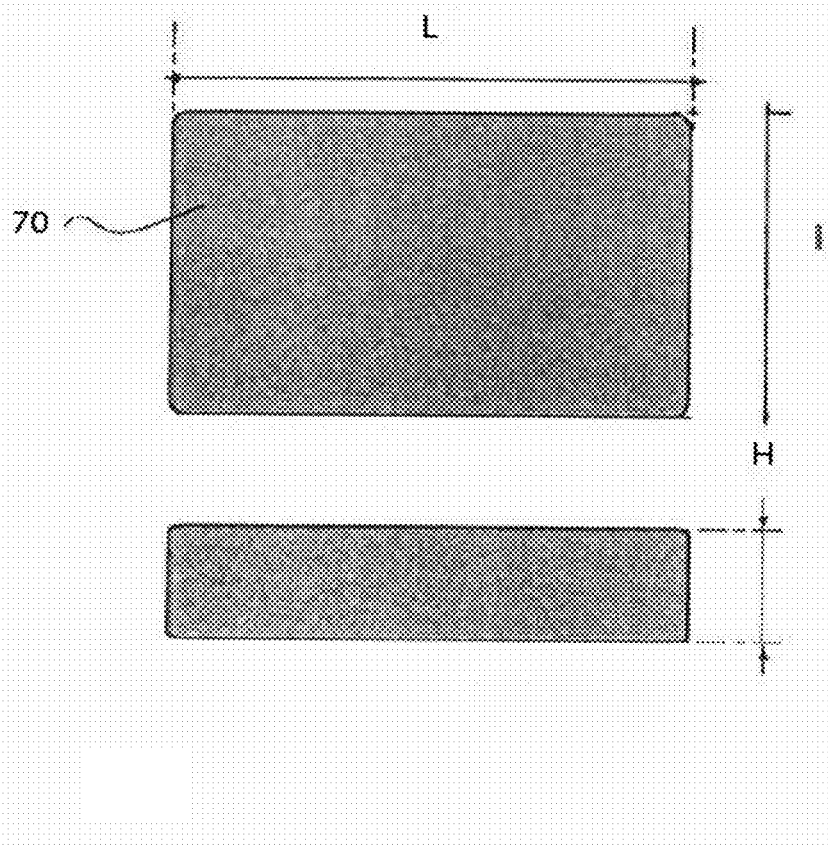
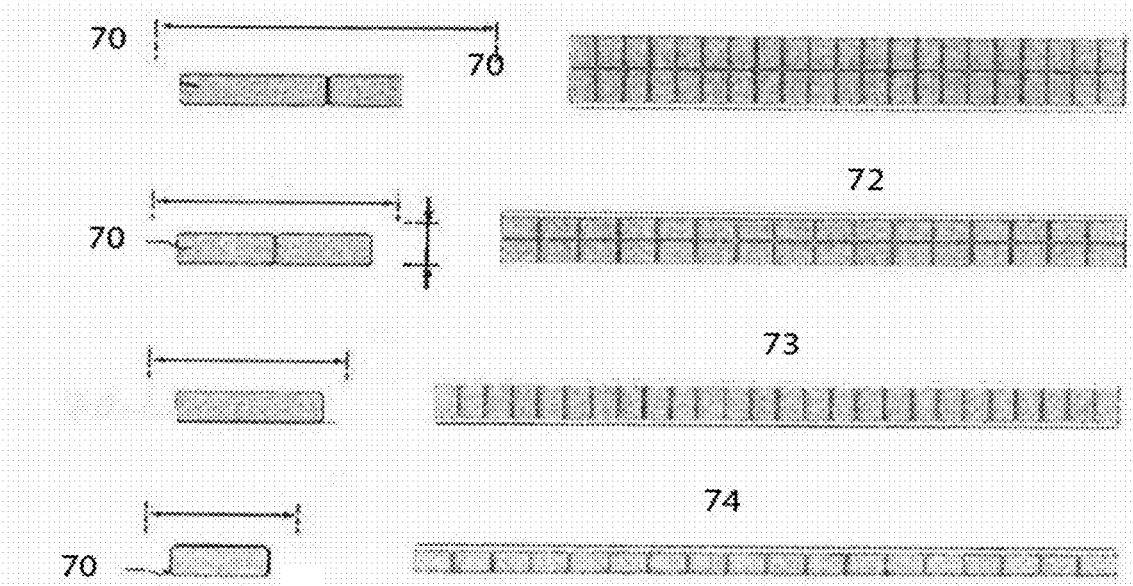
Figure 11

CLOTHING OR ACCESSORY FOR PROTECTION AGAINST IONIZING RADIATION

CROSS-REFERENCE TO RELATED APPLICATIONS

The present application is a continuation-in-part of pending U.S. patent application Ser. No. 15/843,563, filed Dec. 15, 2017, which is hereby incorporated by reference in its entirety. The present application is a continuation of and claims priority from French Patent Application No. 1756381 filed on Jul. 6, 2017, and hereby incorporated by reference in its entirety.

BACKGROUND

The present invention relates to clothing and accessories for protection against ionizing radiation made of two parts, each part containing a magnetic element capable of cooperating with the magnetic element of the other part to allow maintenance of contact, fixation, adjustment or adjustment between said pieces.

SUMMARY

It has a particularly important, although not exclusive, application in the field of radiology. For example, for radiation protection aprons in one or more pieces, protective skirts and gowns, or neck protection collars, all such clothing or accessories containing pieces with removable magnetic elements.

It is known that the magnetic or ferromagnetic elements can be divided into two categories: soft materials, which are easily magnetized (high permeability and reversibly), and hard materials because of strong, long lasting magnetization, which are used as permanent magnets.

In the following, we will use the term magnetic element to indifferently designate an element of soft material or hard material arranged to form what is termed a permanent magnet.

Note that a permanent magnet can be a natural magnet as well as an artificial magnet. In this case, it can therefore be of very variable composition.

BRIEF DESCRIPTION OF THE SEVERAL VIEWS OF THE DRAWINGS

The accompanying figures wherein reference numerals refer to identical or functionally similar elements throughout the separate views, and which together with the detailed description below are incorporated in and form part of the specification, serve to further illustrate various embodiments and to explain various principles and advantages all in accordance with the present invention, in which:

FIGS. 2 and 3 show two embodiments of magnetic elements allowing for sliding of one with respect to the other, usable with the jacket in FIG. 1.

FIG. 10 shows a top view and a side view of an example of a unitary magnet used for the manufacture of magnetic elements according to the invention.

FIG. 11 shows four embodiments of stripes of magnets usable to form magnetic elements for clothing or accessories according to the invention.

DETAILED DESCRIPTION

Figure 1:
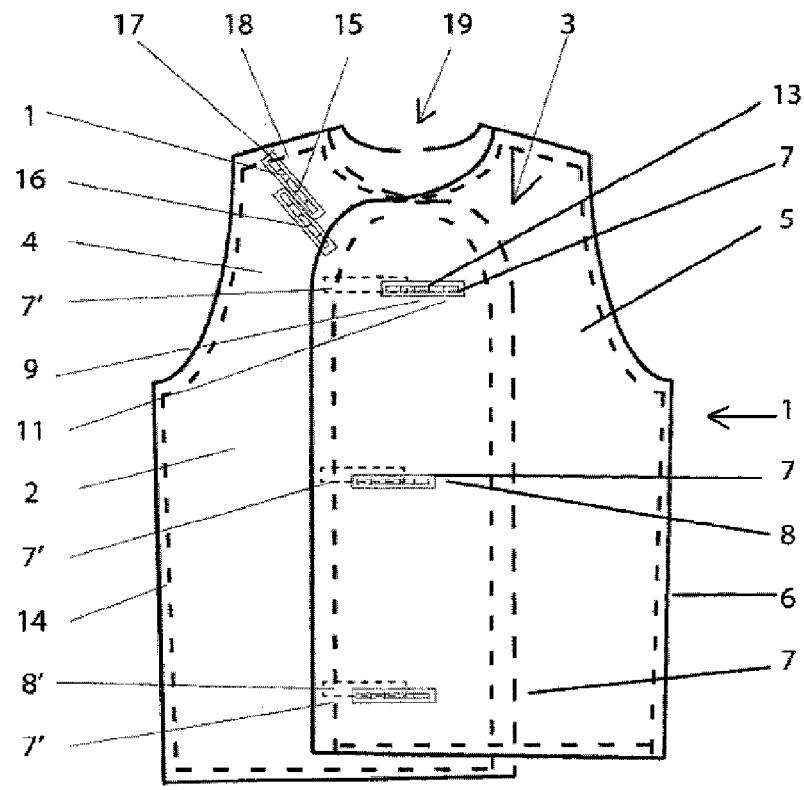
FIG. 1 is a schematic representation of the front view of a jacket according to one embodiment of the invention.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The description of the presently claimed invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Overview

It can be conformed in a simple way, adapted to the usual uses, so as to make it take the magnetization with good stability much more intense and more durable than that of the natural magnets.

Thereafter, mention will also be made of the polarities or poles of or of the magnets that make up the magnetic elements used.

Each magnet has two opposing portions called its poles, namely a positive pole or a north pole (with a tendency to head north) and a negative pole opposite of the south pole.

Through the way they are arranged in the clothing or accessory, the magnet or magnets of a magnetic element of one part is made to co-operate with the magnet or magnets of the magnetic element of the other part through one of its opposite portions.

For the sake of simplicity, we shall hereafter call the magnet, the portion of which is arranged to cooperate with the other, presents the positive pole, a positive magnet, and that which presents the negative pole, a negative magnet.

Devices for contacting, adjusting and/or fixing together parts of clothing are already known, such as dresses, bras or accessories, for example clothing, such as shoes or belts.

Maintaining contact, fine-tuning, adjusting or closure of a garment, shoe or any other accessory is thus traditionally done with the help of button-buttonhole, button-caliper, button press, clasp, facet, eyelet, zipper closure, or through the hooking system known under the trademark "Velcro®".

Such devices, known by some since antiquity, have removable fastening systems comprising male systems and female systems which can be connected to each other and which have disadvantages.

These systems are not in fact easily adjustable, for example forcing the user to undo or remove elements to obtain the correct adjustment.

Moreover, their adjustment will always require precise manual intervention by the user, which is sometimes difficult for some of them, such as the disabled, pregnant women, children or the elderly.

There are also known belts with magnets (U.S. Pat. No. 5,307,582) which, this time around, allow certain adjustment. However, this one is not optimized, while being complicated and expansive to implement.

A garment closing system (FR-A-2 492 938) comprising magnetic elements made of fixed rigid material so as to be spaced on the edges of two ribbons of flexible material also exist.

Similarly, document FR-A-2 005 580 describes a ski boot closure equipped with a magnetic safety preventing its unintentional opening.

But generally speaking, all these known systems that use magnets allow only two parts to be associated in a predetermined position of the male and female elements without a way to instantly modify the location of these elements.

Finally, there are known devices (WO/0013328) that allow such adjustment, and which are generally satisfactory. But these can still be improved. In fact, magnetic elements which are metallic, may in some cases be inconveniently heavy and/or generate a magnetic field whose intensity could still be optimized.

Indeed, in particular for protective clothing which is both heavier and more rigid than conventional clothing, it is understood that the overall weight can be inconvenient and/or that an insufficient fastening which risks inadvertent detachment may present disadvantages.

The present invention seeks to overcome these disadvantages by proposing protective clothing or accessories against ionizing radiation, comprising means for fastening or fitting together their parts, that respond better than those previously known, to the requirements of practice, in particular given that it makes it possible to optimize the weight and the force of the magnets used, in that it creates greater ease of opening and/or closure of the clothing, for example at a distance and/or in a informed manner, by allowing better secure attachment and greater comfort for the user.

The implementation, but also the maintenance (washing, for example) are thus facilitated. People in difficult environments or those who move constantly thus benefit with the invention, of a simple, reliable, inexpensive and easy to use closure.

In the prior art, this type of clothing used by radiologist operators and/or physicians includes Velcro® fasteners.

But the noise of the Velcro® when the operator or the medical practitioner (e.g., doctor, radiologist, dentist, veterinary surgeon) adjusts his clothes can bother or even surprise some patients already weakened by their disease, or frighten animals that can during a radiological procedure, and the Velcro® are easily contaminated and can be hard to decontaminated.

As a reminder, three bacteria represent half of the isolated germs in the context of nosocomial infections:
  *Escherichia coli* (26%), which naturally lives in the intestine of everyone,
  *Staphylococcus aureus* (16%), present in the mucosa of the nose, throat and on the perineum of about 15 to 30% of individuals,
  *Pseudomonas aeruginosa* (8.4%), which develops in soils and in humid environment (faucets, pipes . . . ).

This applies to patients who are hospitalized or come for consultations, but also and permanently to the staff working in contact with contagious patients.

These nosocomial diseases have a significant impact on society, and can lead to complications in the treatment of a patient, or even cause his death.

Some French studies, based on different methodologies show a rate of 6 to 15.7% of death and/or serious diseases in French hospitals are due to this type of infection.

It should be noted that the patient, or his surviving dependents, are rarely compensated and must face this situation alone.

The present invention proposes specifically clothing or accessory for the protection against ionizing radiation comprising an ensemble made of flexible material that can be threaded by an operator, means of reinforced protection comprising one or more layers or protective plates against ionizing radiation integrated within said garment or accessory comprising at least two parts, namely a first part containing at least a first magnetic element and a second part comprising at least a second magnetic element making it possible to set, arrange, adjust or close the garment when one of said first and second parts is activated by the operator to cooperate with the other part, each magnetic element being composed of at least two groups, each having at least one magnet, namely a group of positive magnet(s) and a group of negative magnet(s), the groups with the same magnetic element being set directly or indirectly on one and the same medium and/or between them, and being able to co-operate with the groups from the opposite signs of the other magnetic element.

Such clothing weighing up to 8 kg, the magnets are attached to remain hooked, while allowing very good seal from radiation at the interface between the parts.

The fastening system makes it possible to superimpose the end of the pieces giving a sandwich like structure preventing leaks and/or diffractions of the radiations towards the operator.

It is possible to add a steel plate or strip in order to return the inactive face of the magnets towards the active face of the magnet, this function is commonly called "mirror effect".

By the term integral to the body we mean specifically to be caught between its two walls, for example made of fabric and/or formed by a layer of woven fabric made of lead wool or other metals incorporated in the body, for example made of fibers of synthetic fabrics.

In advantageous embodiments, one or more of the following provisions are also used and/or used:

the magnetic elements glued between them are designed to allow the magnetic elements to be pulled away from one another with a traction force of between 0.5 kg and 20 kg in the direction perpendicular to the plane of the magnets, the articulations between magnets allowing a curvature with a center of curvature located outside the fastener with respect to the operator;

as an advantage, the force is less than 1 kg, for example, between 0.2 kg and 0.4 kg.

Three types of forces are traditionally measured: peeling, sliding and pulling strength;

as an advantage, the force is less than 1 kg, for example, between 0.1 kg and 0.4 kg for the peeling motion;

each magnetic element has at least two magnets per group, the positive magnets of an element arranged alternately with the negative magnets of the same element;

the magnets of the same element are set side by side on a support which is flexible, so as to allow articulation between said magnets;

the magnets of the same element are permanently set to one another by welding or gluing them and/or are formed into one piece with different sectors of magnetization polarity;

the first part comprises a first sleeve in which the first element is inserted and movable, so that a multitude of adjustments or adjustments are possible thanks to the sliding of the first magnetic element within the said first sleeve;

the second magnetic element is itself included and movable in a second sleeve belonging to the second part;

the second magnetic element is fixed to the second part;

the first part and/or the second part of the garment or accessory comprises two sleeves;

the sleeve(s) are reinforced and/or in non-rectangular shape;

one of the first and second parts of the garment at least partly comprises a strap or a sling;

one of the first and second magnetic elements comprises a magnetized belt or strap zone belonging to the corresponding first or second part;

the magnet or magnets of the magnetic element of one part has a concave shape and the magnet or magnets of the magnetic element of the other part has a complementary convex shape of said concave shape;

the clothing includes a way of detecting and signaling the closure or the opening;

the clothing includes a way to trigger an alarm or a command in the event of compliance or otherwise with specific conditions, for example in the event of rupture of the radiation-tight seal between the facing parts.

In one embodiment, the aprons are equipped with magnetic strips comprising alternating positioned magnets, which multiplies the power of each magnet by ten (10).

However, the possibility of placing a band of magnets in front of an articulated rod or a steel strip may also be considered, the tearing force will be less strong, but the magnet/iron contact will work.

The invention also provides a garment for example as described above, characterized in that it is in two parts, namely a jacket provided with a left-hand pane forming a first part and comprising a first portion of the protection means, and a straight section forming a second part and comprising a second portion of the protection means, the two sides being arranged to cover a determined area and to be attached to each other by a plurality of magnetic elements arranged vertically opposite each other along the height of the jacket and an enveloping apron containing another portion of the protection and comprising a so-called the rear side forming a first part and a so-called front side covered making up the second part, the two faces being arranged to overlap each other on the front of the operator and to be attached to each other by at least magnetic elements placed horizontally against each other, for example horizontally over a given width.

The first or second determined surface area is understood to mean a surface area of between 0.1 $m^2$ and 0.5 $m^2$, for example 0.2 $m^2$.

as an advantage, the magnetic elements associated with each other are designed to allow the magnetic elements to be pulled away from one another with a tension force of between 0.1 kg and 0.5 kg in the direction perpendicular to the plane of the magnets, the articulations between magnets enabling a curvature with a center of curvature located towards the exterior of the fixture relative to the operator during pulling.

As an advantage, the force is less than 1 kg, for example, between 0.2 kg and 0.4 kg;

Also, as an advantage, one and/or the other of the arrangements described above can be provided.

The invention also proposes a collar intended to protect the neck of the physician or patient from radiation, characterized by the fact that the collar comprises two movable magnetic elements in a sleeve, which can each be separated by a seam, the closure on the bottom being made by contact between the two magnetic elements.

It also proposes a garment as described above, in the form of a skirt comprising at least two sleeves, and advantageously five, each comprising two magnetic elements, one fixed and one mobile, separated by a seam, each for example, into a millet of rectangular shape the size of the sheath plus a few millimeters and then closing on itself.

The invention also relates to a jacket comprising an adjustment strap which contains one or two magnetic elements, one fixed and/or movable arranged to cooperate with one or more mobile magnetic elements and/or set in facing relationship with the jacket.

The accessory may also be a cap or cap intended to protect the physician or patient from radiation, for example x-rays, comprising four sleeves which each pass in a loop, each sleeve containing two magnetic elements, one fixed and one mobile.

Embodiments

The magnets used in the embodiments of the invention, more particularly described herein, are preferably based on neodyne iron boron of 7.3 to 7.5 g/cm3 in of density compressed, the coating of the magnet being obtainable by an alloy based on nickel, zinc or tin and copper.

One of the difficulties of the present intention was to be able to guarantee the correct operation of the magnets over time.

These high-quality magnetic materials are used in locations where high magnetic force is required and require five times less space than the hard ferrite magnets with the same magnetic power.

An advantageous process for the manufacture of the rare earth-based magnetic materials that can be used with the invention is also, for example, the following.

The various raw materials for alloys are first mixed with high precision, under vacuum or inert gas.

For example, the components are mixed according to the following mass preparations of iron boron neodymium.

The base material can be obtained by melting the constituents or by reduction in a calciothermal route, for example, around 13000 C from a NdFe fluoride compound and $FeCl_3$ iron chloride ($NdF_3+Ca+FeCl_3-<(NdFe)+CaCl_2+CaFe_2$).

The formulation of the magnets used is, for example, as follows:

Coating (covered): Zn+Epoxy

Neodymium: from grade 40 to grade 52:

N40: PRND: 28.8%; This 3%; B: 1%, Al: 0.5%; Cu: 0.2%;

Co: 0.5%; Others (other): Fe

N52: PrNd: 30.5% B: 0.98% Al: 0.1% Cu: 0.12%

Co: 1.5% Ga: 0.15% Nb: 0.2% Zr: 0.1%; remaining (remaining): Fe.

The raw material particles are crushed, until they meet very precise tolerances (grains of the order of 1 micron).

Then, the products are matrix by imposing a powerful magnetic field to direct the metal particles.

Finally, the elements are sintered in special furnaces under vacuum at 1050° C., or under argon.

After rapid cooling, a return to high temperatures (600° C. to 900° C.) is finally carried out, before the cycle is completed by rapid quenching.

The finish is then done by machine tools using sparks or with machines equipped with diamond tools because the final product is very resistant.

Other materials that can be used include the cobalt samarium ($SmCo_5$, $SmCo_7$) and other types of neodymium iron boron ($Nd_2F_{14}B$), which are rare-earth magnetic materials of high efficacy.

In order to avoid the oxidation process, the final product of Neodymium Iron Bore is, for example, galvanized simply (Ni, Sn or Zn) or triple (Ni+Cu+Ni) or Sn (Zn+Cu+Zn).

The magnets can, for their part, be advantageously covered one by one with a protective layer also obtained by galvanizing protection against ionizing radiation (x-rays), for example of polygonal shape adapted to conform to the general shape of the operator's bust and to protect those parts of the human body that are particularly sensitive to radiation (belly, lung, heart, liver, intestines).

As an advantage, the jacket is also reinforced with radiological protections on the back, in case the operator finds himself with his back to the emission of the radiation. The thickness of the protection can be reduced here because of a lower risk of exposure.

The plates include, for example, a polymer comprising particles of radiation-attenuating material (atomic mass greater than 56, for example) which gives the plate a certain flexibility.

The plate may also be formed of closely spaced superimposed sheets and/or contain several different attenuating substances.

What is important is that the protection has enough and sufficient thickness to permit the attenuation of the amount of radiations received by the patient.

The thickness will therefore in particular be a function (in a manner known per se) of the radiation likely to be received, the average exposure time and the absorbing materials used.

In other embodiments, the absorbent support material is semi-solid (resin).

Figure 1A:
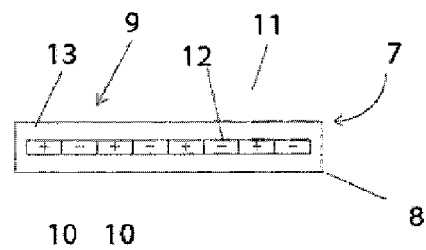
FIG. 1a is an example of a magnetic element that can be used with the invention.

According to the embodiment of the invention more specifically described herein, the jacket comprises a first part or pan 6 containing several identical magnetic elements (for example three) comprising strips 8 provided with at least one group 9 of positive magnets 10 and of a group 11 of negative magnets 12 setup in an articulated manner to one another on the same support 13 (see FIG. 1*a*).

The jacket comprises a second part or pan 14 provided with the same number (3) of magnetic elements 7' (shown in dotted lines in the figure) identical to the elements 7 formed by strips 8', identical to the strips 8 and therefore provided with positive magnets 10 and negative magnets 12 (having a magnet ready location) capable of cooperating with the magnets of opposite signs of the corresponding elements opposite the first part 6.

An integral shoulder tongue 15 provided with a magnetic element 16 as described above makes it possible to complete the closing of one pan on the other by cooperating with a fixed symmetrical magnetic element 17 on the shoulder 18 of the second panel 14.

The neck 19 of the operator may, for in this case, be protected by a collar which will be described hereinafter with reference to FIG. 6.

A further embodiment of the magnetic elements according to the invention has now been described with reference to FIGS. 2 and 3.

FIG. 2 shows a magnetic element or device for holding, adjusting, adjusting or closing parts of clothing or any other accessory comprising a first part 21 comprising at least one sleeve 22 into which a first magnetic element 23 is inserted.

According to one embodiment of the invention, the first magnetic element 23 comprises one or more magnets bonded to each other in an alternate manner, namely (as shown in the figure in a non-limiting manner) a first positive magnet 23' and a first negative magnet 23", and is movable inside the sleeve which comprises, for example, a double strip of 1 cm width of fabric.

The device 20 further contains a second part 24 that contains a second magnetic element comprising two magnets, namely a second part positive magnet 25" and a second negative magnet 25', which will be able to act together with the first opposing polarity magnets 23' and 23".

As shown with reference to arrows 26, the first magnetic element 23 which is of greater width than the width of the sleeve will be able to slide in the sleeve 22 between different positions, a multitude of setting or adjustments being possible.

Given the two polarities presented on the same magnetic element, the attachment of the parts to each other is more solid, and curiously with equal magnetic weights and fields, both stronger and easier to undo than unipolar magnets.

The magnets of each magnetic element are set, for example, by gluing them to a support (not shown), which is flexible, for example made of plastic material, which enables them to be articulated together according to an advantageous embodiment of the invention.

FIG. 3 shows a second embodiment of a magnetic element or device 27 according to the invention comprising two sleeves 28 and 29 in parallel, comprising, for example, channels or vent of fabric of the same width and of greater length, the said ducts being situated or liable to be placed opposite each other during the implementation of the device, to close or adjust two open parts of clothing.

These two sleeves 28 and 29 respectively belong to a first and a second part of the device 27 to which they are fixed.

The sleeves 28 and 29 each comprise a magnetic element 30 and 31 each constituted by two opposing polarity magnets, which are provided on a support (not shown), namely a positive magnet 30', 31" and a negative magnet 30" respectively, and 31', the two elements being able to work with one another in order to allow a double adjustment, which is advantageous, for example, in certain embodiments of the belts of the apron or of the radiological skirt.

A magnetic element is a set of magnets joined together by magnetic contact or by gluing to form a magnet "block". These generally parallelepiped magnets are joined by the edge (the smallest area of the parallelepiped). The assembly thus obtained is not very stable. Indeed, when they are not set together by more rigid means, a movement or a shock enters the magnets to position themselves on each other by way of the larger surface of the parallelepiped.

Figure 4:
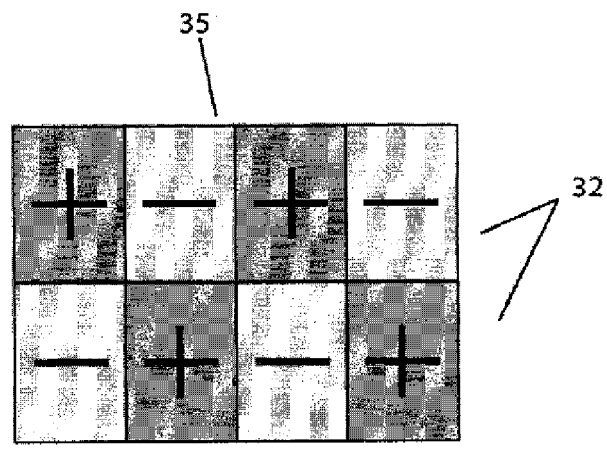
FIGS. 4a to 4c show another embodiment of the magnetic elements that can be used with a garment or an accessory according to the invention, comprises blocks of substantially square magnets formed with small positive/negative/positive magnets unit articulated with the help of a flexible elastomer type link.
Figure 4:
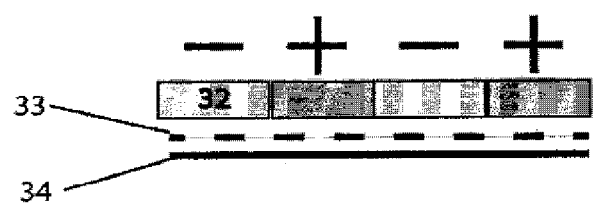
Figure 4:
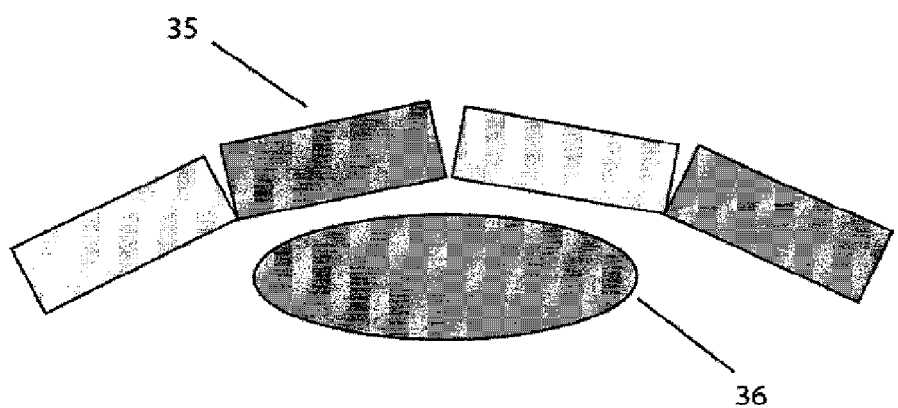

According to an advantageous embodiment of the invention described with reference to FIGS. 4a to 4c, the magnets 32 are assembled together by contact lateral (on the smallest side of the magnet) and to form a multipolar block.

The magnets 32 are held together by magnetic contact and by a special adhesive 33 of known type which adheres to the surface of the magnets.

As an advantage, a plastic or canvas support 34 is provided, for example consisting of a canvas and/or plastic film (see FIG. 4b) glued on the lower face of the magnets (glue as dash in the figure).

As a result, an assembly consisting of three layers is obtained; first, the magnets 32 second the adhesive 33 and, third, the support 34.

A steel strip may be added after the support in order to obtain a "mirror effect".

The strip may be made of a single block, for example substantially parallel to one another or comprising a stack or at least a partial parallel stacking of at least two steel sheets, for example greater than or equal to three sheets, for example greater than or equal to four leaves.

The steel sheets are, for example, substantially parallelepipedal.

In one embodiment, each element magnetic has a strip, placed parallel to the magnets and each on the opposite side of the opposite side of said magnets when they are arranged as closed.

The strip is for example of a thickness substantially equal to that of the magnets, for example between 70% and 130% of the thickness of the magnets, for example between 80% and 120%, for example between 90% and 110%.

In the embodiment where the strip is made in several sheets, these may be integrated with one another or may cooperate with one another in a soft or sliding friction on their parallel faces.

It is, for example, possible to facilitate the sliding of the sheets between themselves by applying, prior to their positioning in the clothing or accessory, a layer of lubricant, for example oil, such as, for example, silicone oil or a substance pulverulent, such as talc.

The whole thing allows an articulation 35 in blocks. Let us specify that the magnetic element or block may comprise 2, 4, 6 magnets or as much as necessary.

The articulated block presents an important advantage because it will in particular be able to adapt to rounded shapes or organs 36 (see FIG. 4c).

It also allows the magnets to be maintained in the same condition.

As an advantage, when the magnets are arranged vertically, the blocks are bent vertically.

In this case, vertical rectangular parallelepiped magnets are used, each magnet being adhesive (by magnetic contact) to the adjoining magnet by the longest dimension; the end-to-end magnets therefore constitute a vertically flexible block. This is the embodiment more particularly reproduced in FIG. 4.

Figure 5:
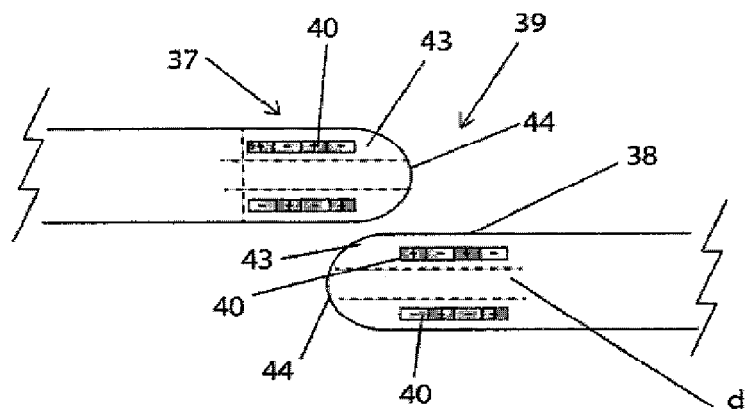
FIGS. 5a, 5b and 5c show views from above, three embodiments of magnetic elements for a belt according to the invention enabling a very robust closure.
Figure 5:
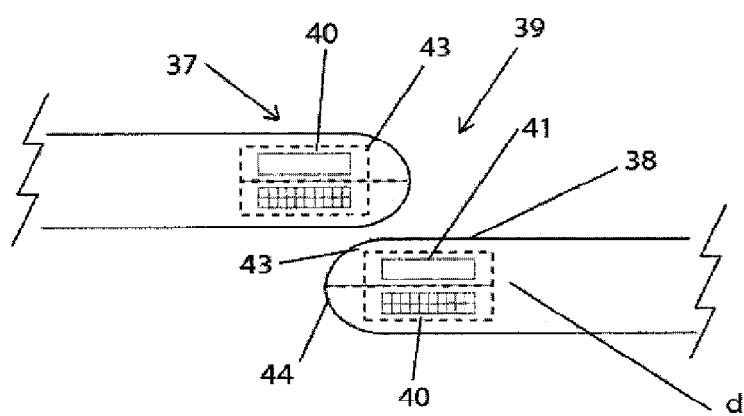
Figure 5:
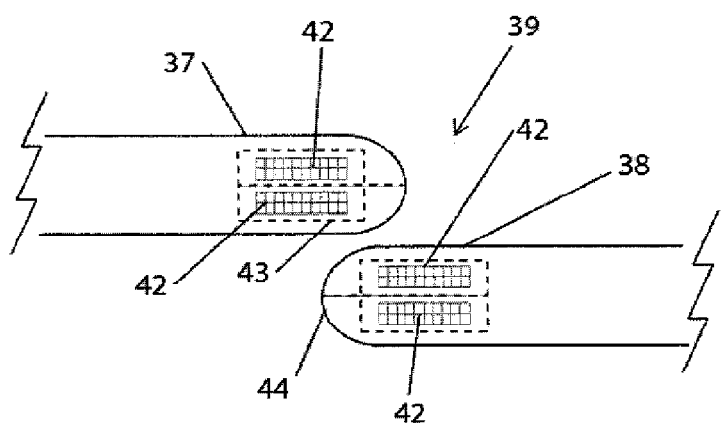

FIGS. 5a to 5c show three examples of the arrangement of magnetic elements in an accessory according to the invention.

More precisely, each figure represents a pair of end portions, 37, 38 of belt or band 39, for example 15 cm to 20 cm wide, forming the first and second parts of the accessory according to the invention.

Each magnetic element 40, 41, 42 is placed in a sleeve 43, the sleeves being (FIG. 5a) or not (FIGS. 5b and 5c) separated by a distance, for example equal to the width of the sleeve.

The magnetic elements are formed by a row of alternating magnets (FIG. 5a) of two rows of alternating magnets side by side (FIG. 5c) or a combination of the two (FIG. 5c).

Any other arrangement is obviously possible, in particular in sleeves where the magnets slide and/or are more or less distant from the end 44 of the end portion.

Figure 6:
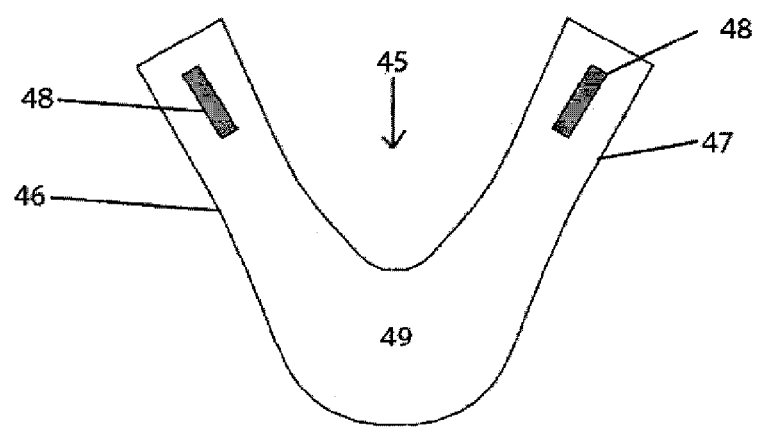
FIGS. 6, 7, 8 and 9 schematically show embodiments of clothing or accessories according to the invention, seen from above (FIG. 6), in section (FIG. 7) of the face (FIG. 8), and perspective (FIG. 9).

FIG. 6 shows a collar 45 made of protective (absorbing) material of ionizing radiation, the two free end portions 46 and 47 of which comprise the identical magnetic elements 48, but has decal magnets of one place, for example sewn into the illustrated sleeves.

These two portions overlap one another when the removable collar is placed around the neck of the operator and are separated by a central enlarged portion 49 in order to protect specifically the thyroid of the operator.

Figure 7:
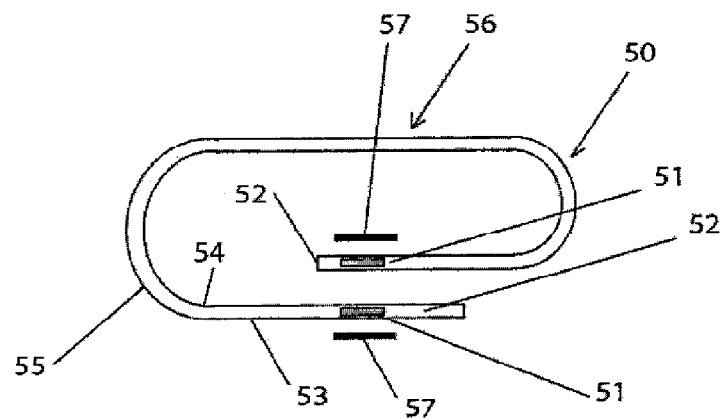

FIG. 7 schematically shows in section a belt 50 comprising magnetic elements identical 51 (with decal magnets) facing each other in the end portions 52 comprising two inner 53 and outer 54 walls, for example of fabric, inside which a material 55 of the radiation shield is inserted on a thickness, for example constant, but which can be attenuated in the back 56.

Protective plates 57 for protecting the magnetic field of known type may also be provided on both sides of the magnetic elements, on the opposite side to that of the interaction.

Figure 8:
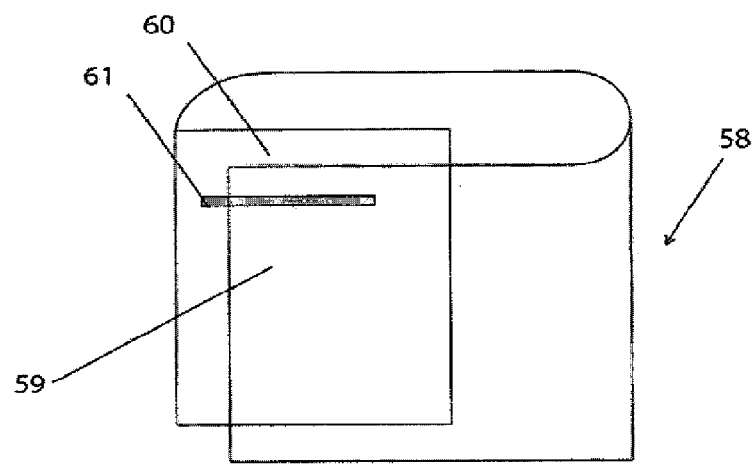

FIG. 8 schematically shows a skirt 58 provided with two panels 59, 60, the interaction of the magnetic elements 61 (shown in the figure at the waist).

Figure 9:
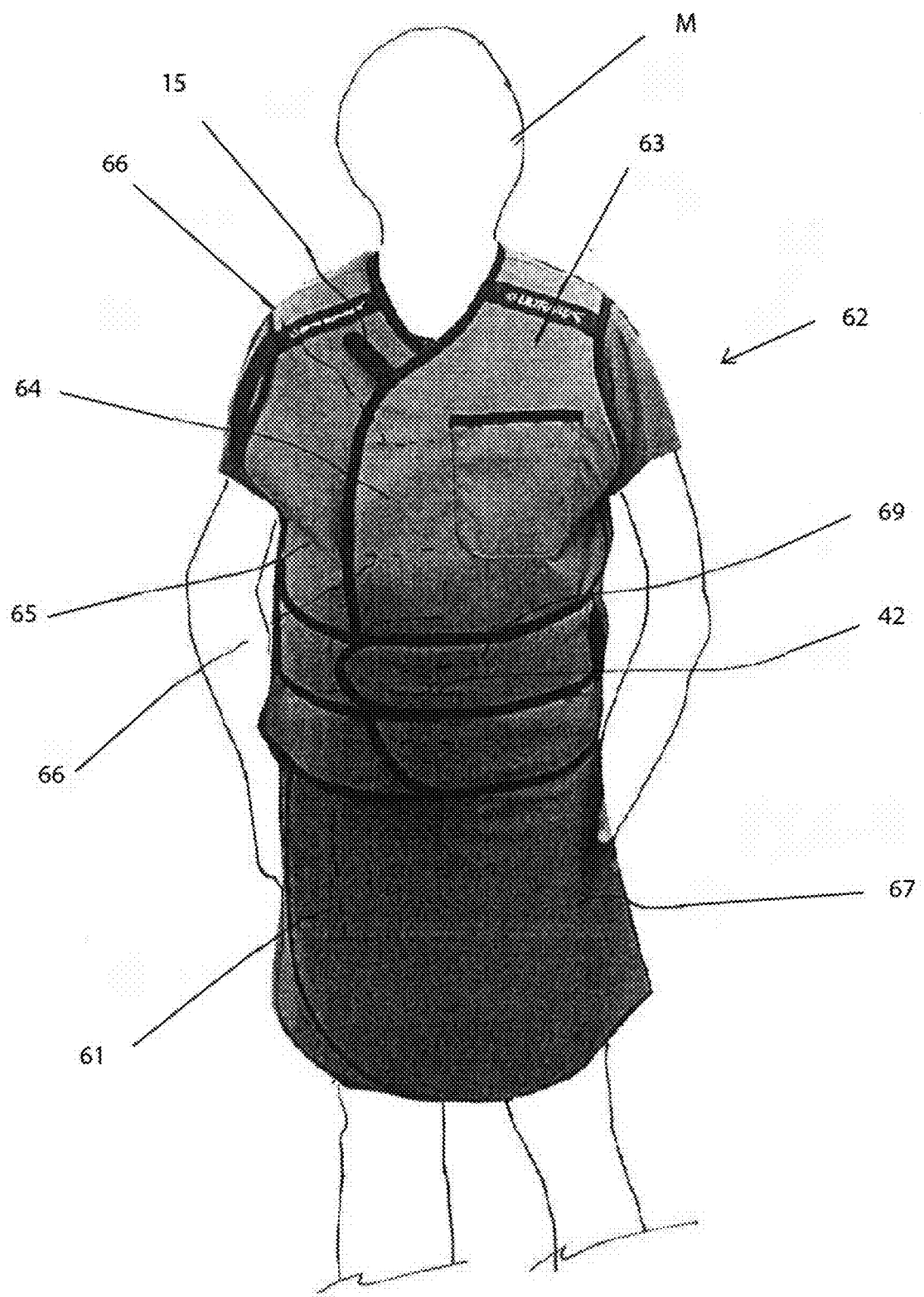

FIG. 9 shows a garment 62 according to one of the embodiments of the invention comprising a jacket 63 provided with a left pan 64 and comprising a first portion of protective means and a portion 65 comprising a second portion of protection means, the two sides being arranged to overlap on a determined surface and to be fixed to each other by means 66 (in broken line in the figure) bands 8 and 8' as described with reference to the figure.

It also comprises a skirt 67 for example as described with reference to FIG. 8 but with magnetic fixing elements 68 disposed and a belt 69 of the type described in FIG. 7 with magnetic elements 42 such as those described with reference to FIG. 5c.

FIG. 10 shows an example of a unitary magnet 70 used with the invention.

It is of the neodymium iron boron type (for example parallelepipedal of dimensions 6×4×1.5 mm) used to make the strips of magnets, for example of FIG. 11.

FIG. 11 shows, by way of example, four embodiments of the strip of magnets which can be used with the invention.

A first type 71 which corresponds to two lines of magnets is placed side by side in a vertical manner (with, for example, L=14 mm and H=2.00 mm), a second type 72 which corresponds to two lines of magnets placed side by side (with, for example, L=10 mm and H=2.00 mm), a third type 73 corresponds to a line of magnets placed side by side in a horizontal manner (with, for example, L=8 mm and H=2.00 mm) and a fourth type 74 which corresponds to a line of magnets placed side by side in a horizontal manner (with, for example, L=6 mm and H=2.00 mm).

We are going to now describe the use of a radiation protection suit according to the invention will now be described with particular reference to FIG. 9. The medical radiologist M, who is going to be doing radios on many sham patients, has to protect himself against ionizing radiation. To do this, examinations are essentially prepared remotely, behind fixed and/or mobile protection screens. This is not entirely satisfactory since the operator cannot completely avoid being in the presence and/or subjected to radiation when he is forced to move.

With a garment according to the invention, it will have the ability to avoid doses of radiation that are too large (that as a reminder are cumulative).

The operator, before performing his work, simply puts on his clothes and/or blouse, the protective skirt 67 which surrounds his hips and attaches magnetically at 68, then threads the jacket 63 (or waistcoat) which panels he has just close 64, 65 one over the other, the latter locking themselves magnetically via the elements 66.

It then closes the belt 69 which locks magnetically with the magnetic elements 42, thus bringing a perfectly leak-proof protection to the assembly.

As is self-evident and as is apparent from the foregoing, the present invention is not limited to the embodiments more specifically described. On the contrary, it embraces all the variants and in particular those where the clothing is of different shapes, and/or where the protective materials against radiation are different.

Figure 12:
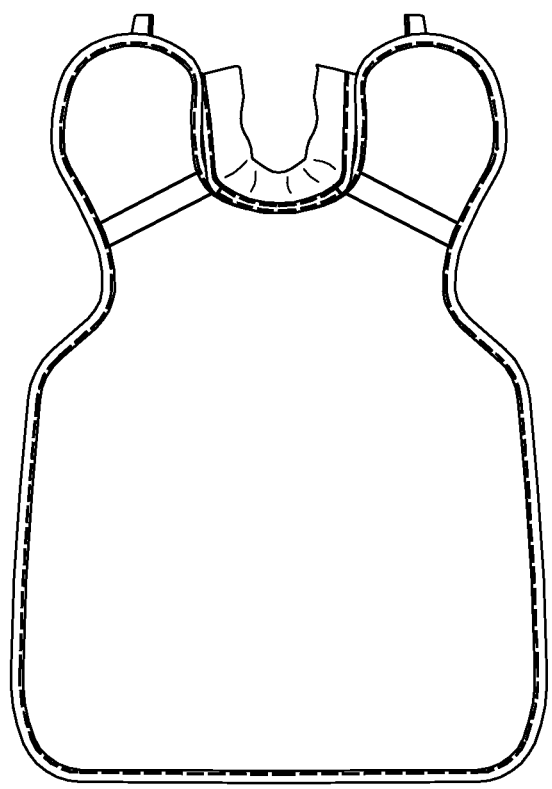
FIG. 12 is a front plan view of a dental apron in accordance with one embodiment of the invention.

FIG. 12 is a front plan view of a dental apron in accordance with one embodiment of the invention.

Figure 13:
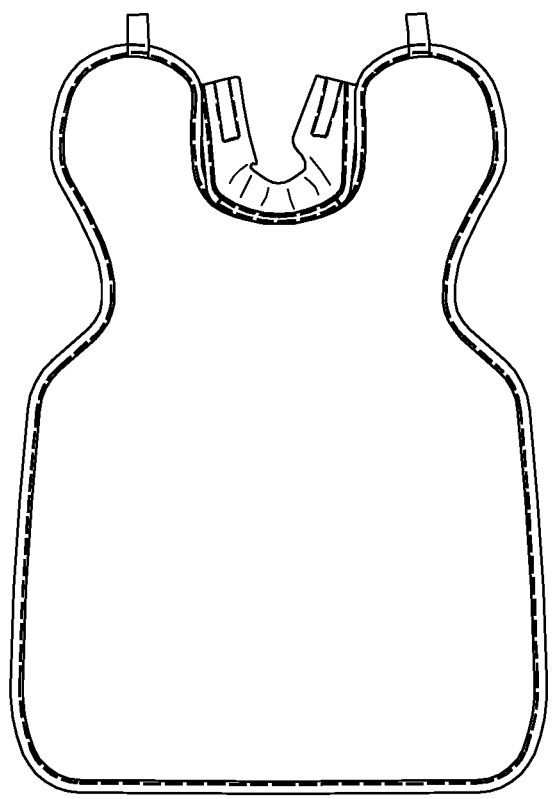
FIG. 13 is a back plan view of the dental apron of FIG. 12.

FIG. 13 is a back plan view of the dental apron of FIG. 12.

Figure 14:
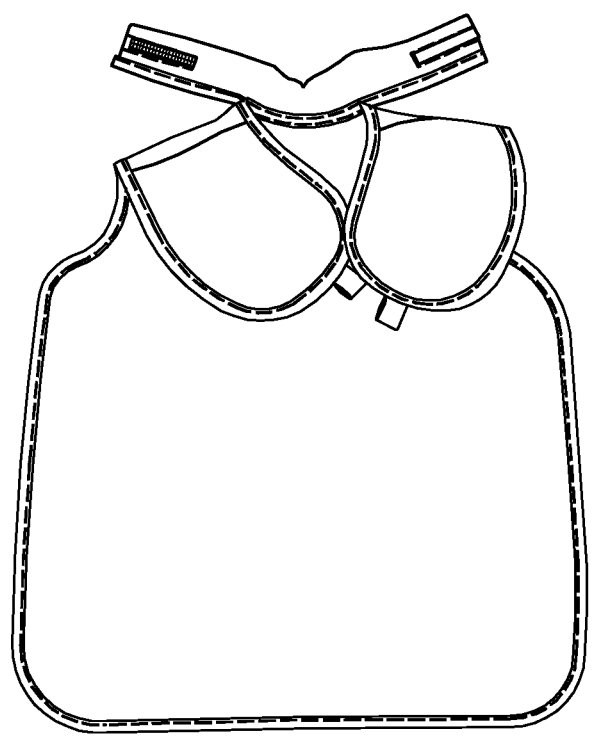
FIG. 14 is a substantially back view of the dental apron of FIG. 12 with shoulder flaps folded over the back and with neck flaps extended showing locations of groups of magnets in the neck flaps, in accordance with one embodiment of the invention.

FIG. 14 is a substantially back view of the dental apron of FIG. 12 with shoulder flaps folded over the back and with neck flaps extended showing locations of groups of magnets in the neck flaps, in accordance with one embodiment of the invention. The groups of magnets are sewn underneath the fabric material of the dental apron. Each group of magnets constitutes a magnetic element. FIG. 14 shows a first magnetic element and a second magnetic element.

Figure 15:
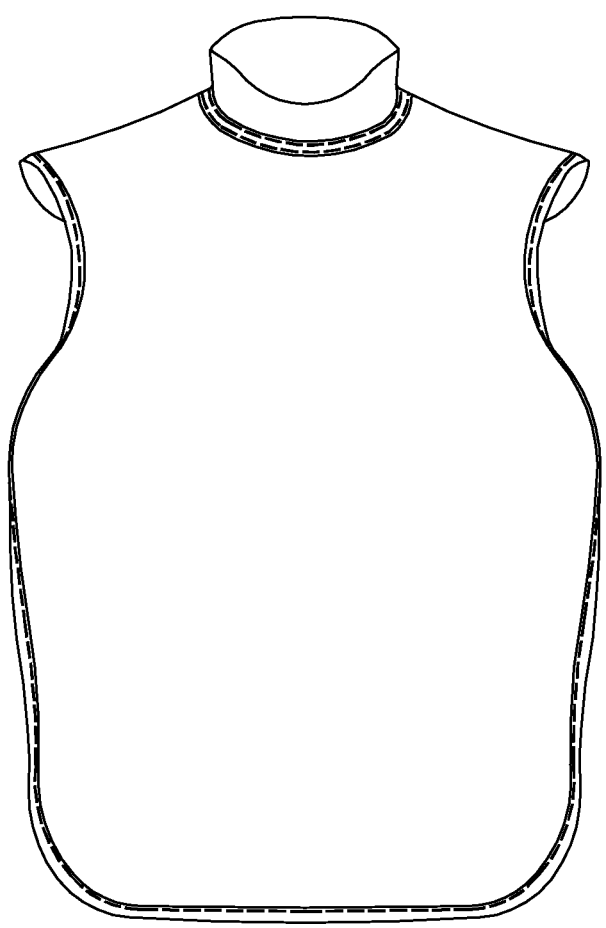
FIG. 15 is a front plan view of the dental apron of FIG. 12 as it would appear being worn by a person.

FIG. 15 is a front plan view of the dental apron of FIG. 12 as it would appear being worn by a person.

Figure 16:
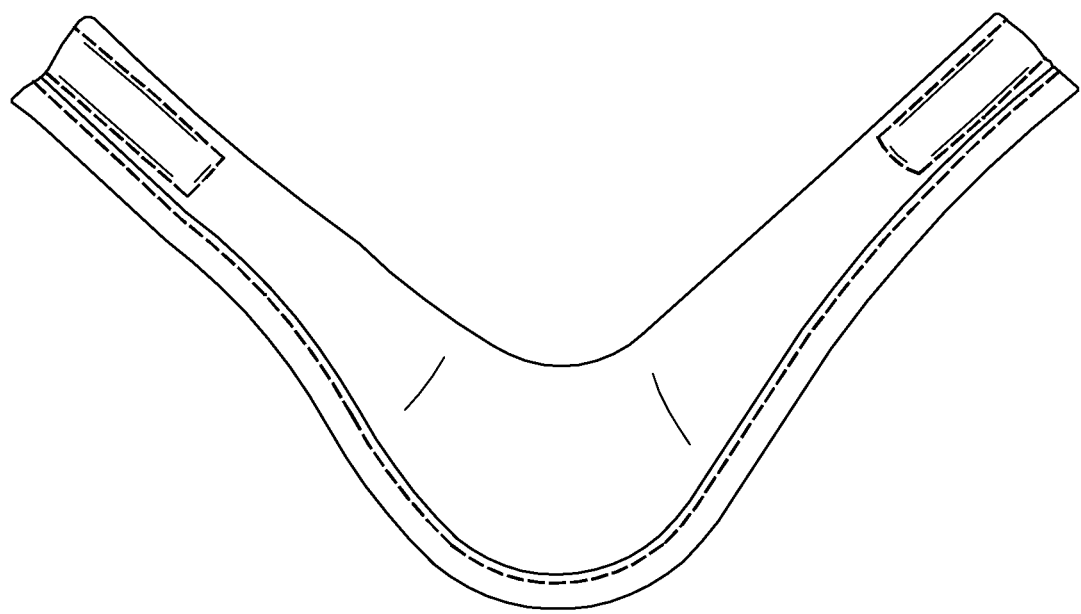
FIG. 16 shows a front plan view of a thyroid collar in accordance with one embodiment of the invention.

FIG. 16 shows a front plan view of a thyroid collar in accordance with one embodiment of the invention.

Figure 17:
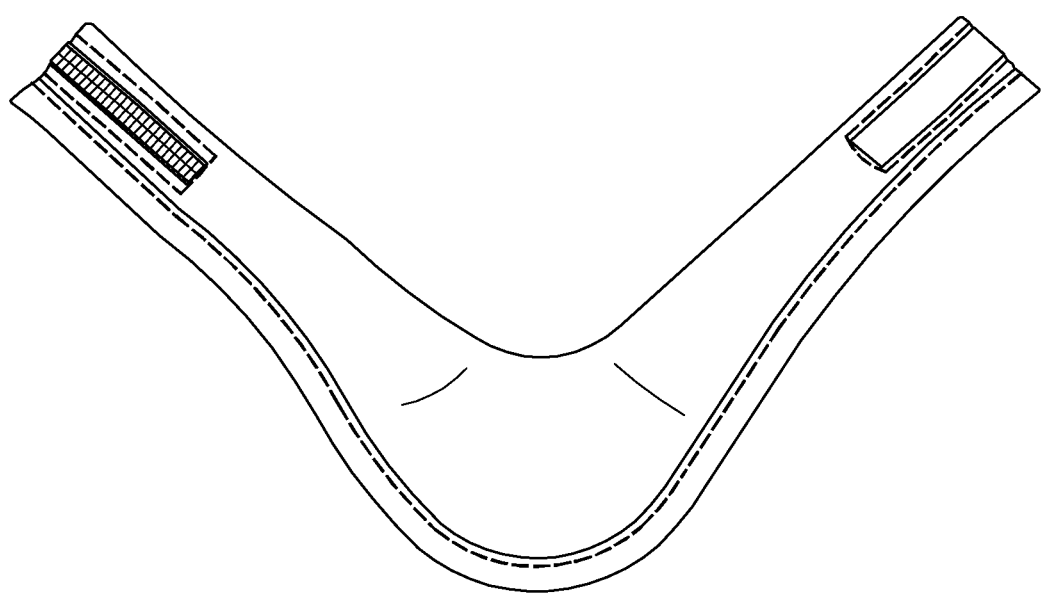
FIG. 17 shows a back plan view of the thyroid collar of FIG. 16 showing locations of groups of magnets.

FIG. 17 shows a back plan view of the thyroid collar of FIG. 16 showing locations of groups of magnets. The magnets of the group of magnets at the left side of FIG. 17, e.g., first magnetic element, are visible. A flexible elastomer binder is under the group of magnets and therefore the flexible elastomer binder is not visible at the left side of FIG. 17. On the other hand, another flexible elastomer binder is visible at the right side of FIG. 17. The magnets of the group of magnets at the right side of FIG. 17, e.g., second magnetic element, are not visible because they are under the flexible elastomer binder at the right side of FIG. 17.

Figure 18:
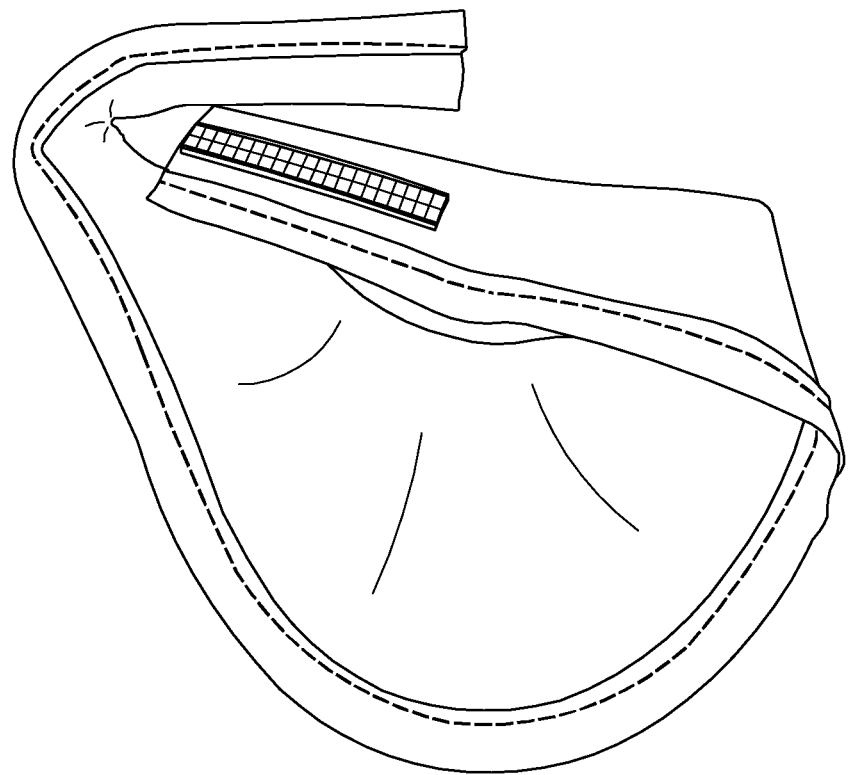
FIG. 18 is a substantially back view of the thyroid collar of FIG. 16 with flaps folded.

FIG. 18 is a substantially back view of the thyroid collar of FIG. 16 with flaps folded suggesting how magnets of opposite plurality would net face-to-face when the flaps of the thyroid collar are brought together by a person after the person places the thyroid collar around the person's neck.

Figure 19:
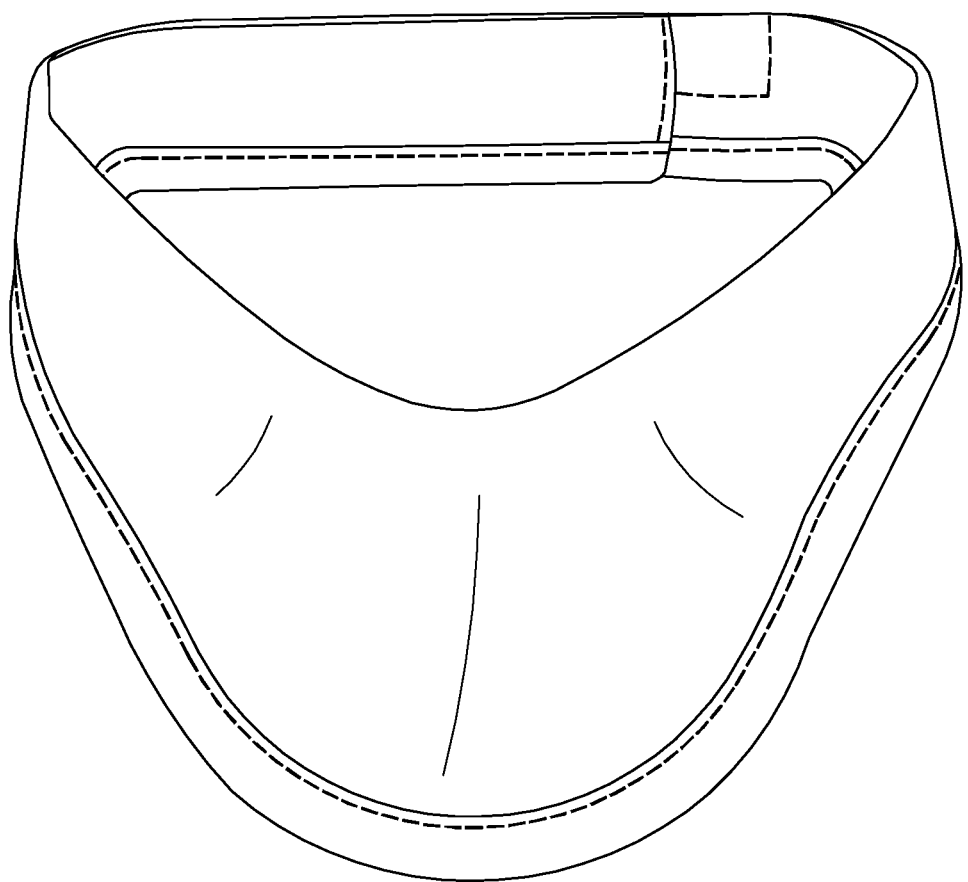
FIG. 19 is a substantially front view of the thyroid collar of FIG. 16 as it would appear when worn by a person.

FIG. 19 is a substantially front view of the thyroid collar of FIG. 16 as it would appear when worn by a person.

Figure 20:
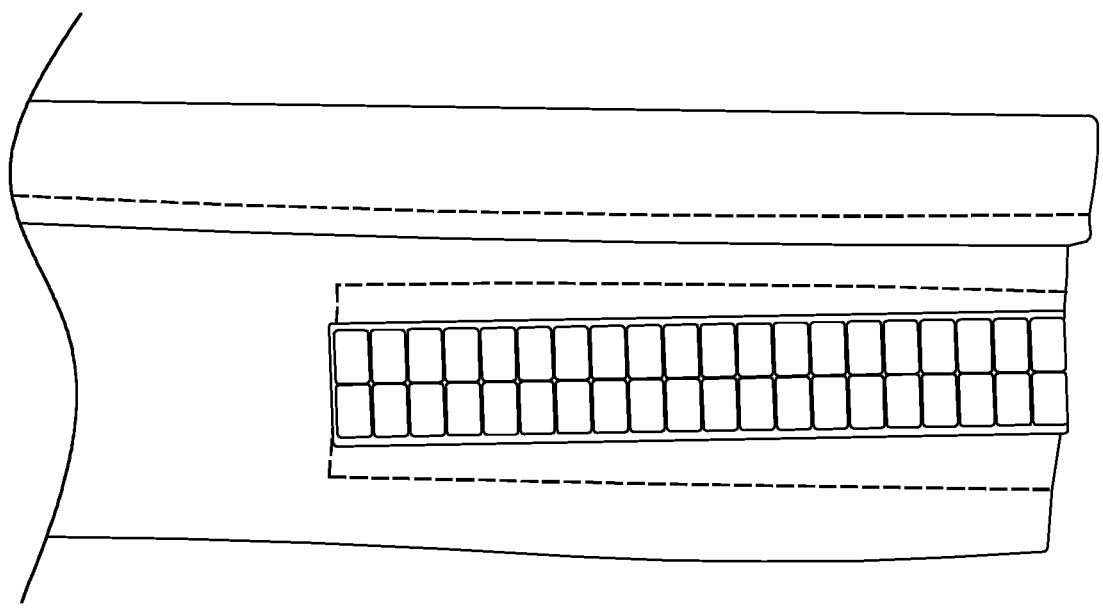
FIG. 20 is a close-up view of an end of one flap of the thyroid collar of FIG. 16 showing forty (40) individual magnets in one of the groups of magnets.

FIG. 20 is a close-up view of an end of one flap of the thyroid collar of FIG. 16 showing forty (40) individual magnets in one of the groups of magnets.

Figure 21:
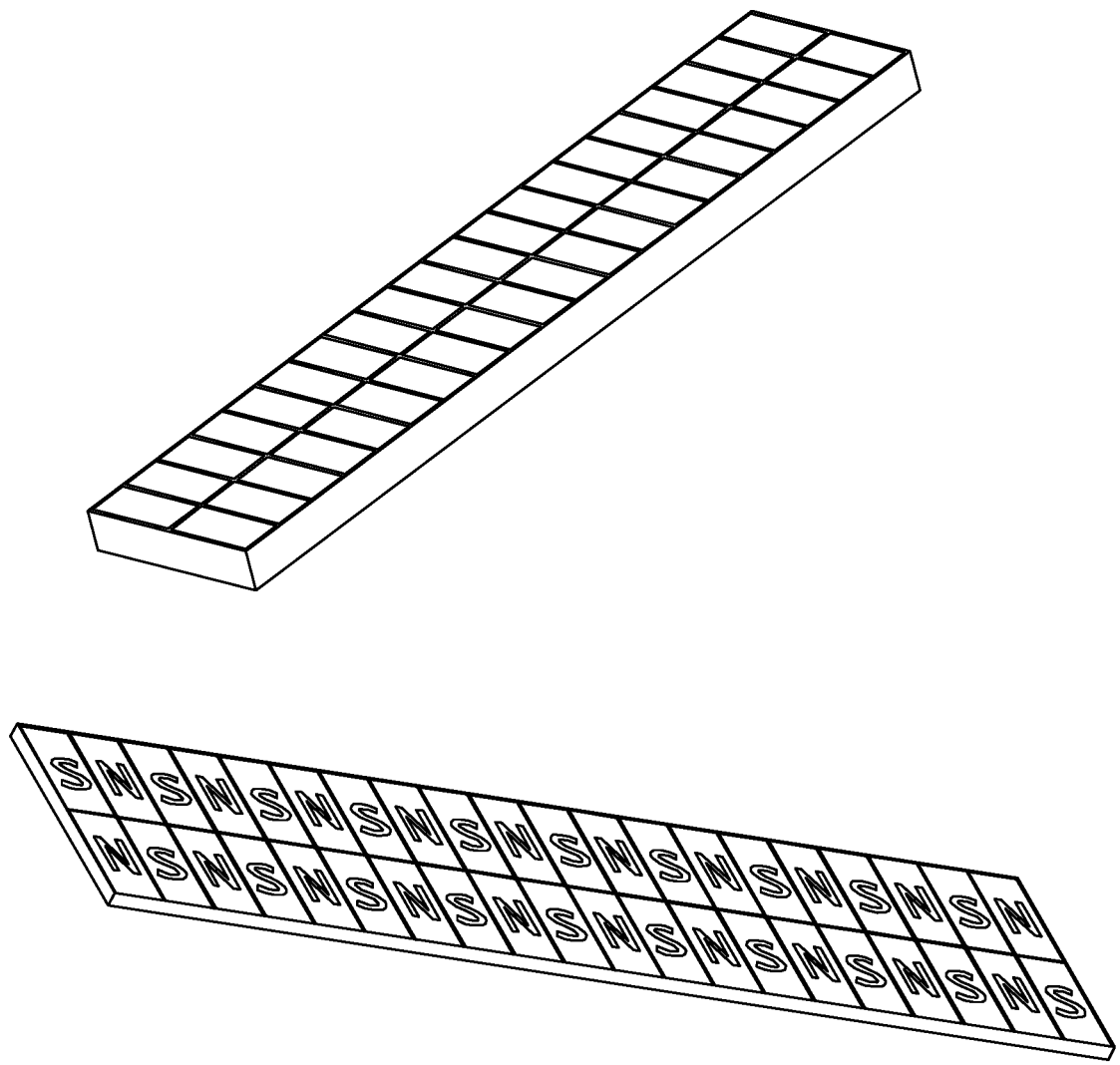
FIG. 21 are perspective views of forty (40) individual magnets of alternating polarity attached to a polyurethane strip to form one group of magnets of the two groups of magnets of the dental apron of FIG. 12 and the thyroid collar of FIG. 16.

FIG. 21 are perspective views of forty (40) individual magnets of alternating polarity attached to a polyurethane strip to form one group of magnets of the two groups of magnets of the dental apron of FIG. 12 and the thyroid collar of FIG. 16. FIG. 21 shows an articulated magnetic block comprising small end-to-end magnets attached to the flexible elastomer binder. In one embodiment, the flexible elastomer binder is a polyurethane base. This configuration allows alternating polarities, giving the closure a power eight to ten times as much as a single large magnet of equal volume. The magnets are placed end-to-end in two rows and stuck to a polyurethane base using a silicone glue specifically suited for the application. The magnets are treated against corrosion and oxidization through a specific coating which gives them a good resistance to the external and harsh environmental conditions.

Non-Limiting Examples

The terminology used herein is for the purpose of describing particular examples only and is not intended to be limiting of the invention. As used herein, the singular forms "a", "an" and "the" are intended to include the plural forms as well, unless the context clearly indicates otherwise. The term another, as used herein, is defined as at least a second or more. The terms "including" and "having" as used herein, are defined as comprising (i.e., open language). The term "coupled" as used herein, is defined as "connected" although not necessarily directly.

The description of the present application has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A garment or accessory for protecting an operator against ionizing radiation comprising:
   flexible material including plates for protecting against ionizing radiation, the plates including a polymer comprising particles of radiation-attenuating material, the flexible material including:
   a first part provided with at least one first magnetic element including magnets and a second part comprising at least one second magnetic element including magnets making it possible to fix, set or close the garment or the accessory and making it possible for the at least one first magnetic element and the at least one second magnetic element to resist sliding relative to each other when one of said first and second part is activated by the operator to cooperate with the other part, each magnetic element being composed of a group of positive magnets and a group of negative magnets placed on a support and being able to co-operate with groups of opposing polarity magnets of the other magnetic element, wherein the magnets are arranged to allow the at least one first magnetic element and the at least one second magnetic element to be pulled away from one another upon application of a force of between 0.1 kg and 20 kg in a direction perpendicular to a plane of the at least one first magnetic element.

2. The garment or accessory of claim 1, wherein the supports are flexible to allow articulation between magnets thereby allowing a curvature with a center of curvature situated towards the outside of the supports with respect to the operator.

3. The garment or accessory of claim 1, wherein each element comprises at least two magnets per group, the positive magnets of a magnetic element being arranged alternately with the negative magnets of the same magnetic element.

4. The garment or accessory of claim 1, wherein the magnets of the same magnetic element are placed side by side on the support.

5. The garment or accessory of claim 3, wherein the magnets are placed on the support in an irremovable manner by welding or gluing and/or are formed in one piece.

6. The garment or accessory of claim 1, wherein the first part is provided with at least one first magnetic element including magnets having a concave shape, and wherein the second part is provided with at least one second magnetic element including magnets having a convex shape that is complimentary of said concave shape.

7. The garment or accessory of claim 1, wherein the first part includes a first sleeve within which the at least one first magnetic element is slidable to allow adjustment of the garment prior to one of said first and second part being activated by the operator to cooperate with the other part, and wherein the second magnetic element is movable in a second sleeve belonging to the second part.

8. The garment or accessory of claim 1, including
a jacket provided with a left pane forming a first portion and comprising a first portion of the protection means and a straight portion forming a second portion and comprising a second portion of the protection means, the two portions being arranged to overlap on a determined surface and to be set to one another by several of said magnetic elements disposed vertically opposite the length of the jacket, and
an enveloping apron provided with another portion of the protection means and comprising a rear face forming a first part and a covered front face as a second part, the two faces being arranged to overlap each other on the front of the operator and to be attach to each other by means of two magnetic elements arranged horizontally opposite one another.

9. The garment or accessory of claim 1, wherein the garment is to protect the neck of a physician or patient from radiation and comprises two magnetic elements movable in a sheath, each separated by a seam, and agencies for cooperating one with the other to ensure the closure of the collar at the bottom by contact between the two magnetic elements.

10. The garment or accessory of claim 1, wherein the garment is a skirt comprising at least between two and five sleeves, each comprising two magnetic elements, one fixed and one mobile, separated by a seam, each sleeve passing through a sleeve of rectangular shape, the size of the sheath plus a few millimeters and then closing on itself.

11. The garment or accessory of claim 1, wherein the garment is a jacket comprising an adjustment strap which contains two magnetic elements, one fixed and one mobile, arranged to cooperate with facing magnetic elements integral with the rest of the jacket.

12. The garment or accessory of claim 1, wherein the magnets are arranged to allow the at least one first magnetic element and the at least one second magnetic element to be pulled away from one another upon application of a force of between 0.1 kg and 1 kg in a direction perpendicular to a plane of the at least one first magnetic element.

13. The garment or accessory of claim 1, wherein the garment or accessory is a dental apron.

14. The garment or accessory of claim 1, wherein the garment or accessory is a thyroid collar.

15. The garment or accessory of claim 1, wherein the particles have an atomic mass greater than 56.

* * * * *